United States Patent [19]

Burtscher et al.

[11] Patent Number: 4,959,010

[45] Date of Patent: Sep. 25, 1990

[54] AUTOMATICALLY REGULATED COMBUSTION PROCESS

[75] Inventors: Heinz Burtscher; Andreas Schmidt-Ott; Hans-Christoph Siegmann, all of Zurich, Switzerland

[73] Assignee: Matter & Siegmann AG, Wohlen, Switzerland

[21] Appl. No.: 642,346

[22] Filed: Aug. 20, 1984

[30] Foreign Application Priority Data

Aug. 24, 1983 [DE] Fed. Rep. of Germany ....... 3330509

[51] Int. Cl.$^5$ .............................................. F23N 5/00
[52] U.S. Cl. ..................................... 431/12; 431/78; 324/464; 250/283; 55/102
[58] Field of Search ................. 431/12, 76, 78, 79; 324/464; 250/373, 423 P, 283, 504; 55/151, 154, 102; 436/35, 55, 137, 905

[56] References Cited

U.S. PATENT DOCUMENTS

| | | | |
|---|---|---|---|
| 2,005,036 | 6/1935 | Howe | 436/137 |
| 2,950,387 | 8/1960 | Brubaker | 250/423 P |
| 3,087,113 | 4/1963 | Foster | 324/464 |
| 3,178,930 | 4/1965 | Moore et al. | 324/464 |
| 3,449,667 | 6/1969 | Gourdine | 324/464 |
| 3,881,111 | 4/1975 | Stephens et al. | 250/383 |
| 4,377,749 | 3/1983 | Young | 250/423 P |
| 4,509,912 | 4/1985 | van Berkum | 431/76 |
| 4,574,004 | 3/1986 | Schmidt-Ott et al. | 55/4 |

FOREIGN PATENT DOCUMENTS 2211720 11/1972 Fed. Rep. of Germany .
2537199 1/1976 Fed. Rep. of Germany .

OTHER PUBLICATIONS

"Photoelectron Emission from Small Particles Suspended in Air", Appl. Phys. Lett. 32(11), Jun., 1978.
Photoelectric Charging and Detection of Ultrafine Particles, "Atmospheric Environment", 1983, vol. 17, No. 3, pp. 655–657.
Probing Aerosols by Photoelectric Charging, H. Burtscher, et al., "J. Appl. Phys.," 53(5), May 1982, pp. 3787–3791.
Dynamic Behavior of Aerosols, Charles E. Billings, et al., "Handbook on Aerosols", Technical Information Center, Energy Research and Development Administration, 1976, pp. 40–59.

*Primary Examiner*—Noah P. Kamen
*Attorney, Agent, or Firm*—Tarolli, Sundheim & Covell

[57] ABSTRACT

In a combustion process a fuel is mixed with an oxygen-containing gas in an adjustable ratio. This fuel-gas-mixture is burned and thereby an exhaust gas is produced. At least a part of the exhaust gas is collected and exposed to an ultra violet radiation source, thereby generating positive and negative charge carriers in the exhaust gas by means of a photoelectric charge separation process. The kind or amount of the positive and/or negative charge carriers is detected to produce a measurement value which reflects the amount and/or the charge of the carriers. Therefrom a control signal is derived and the mixture-ratio of the oxygen-containing gas and the fuel, the so-called λ-factor, is adjusted in response to said control signal in order to improve the efficiency of the combustion and to reduce the emission of toxic substances.

9 Claims, 1 Drawing Sheet

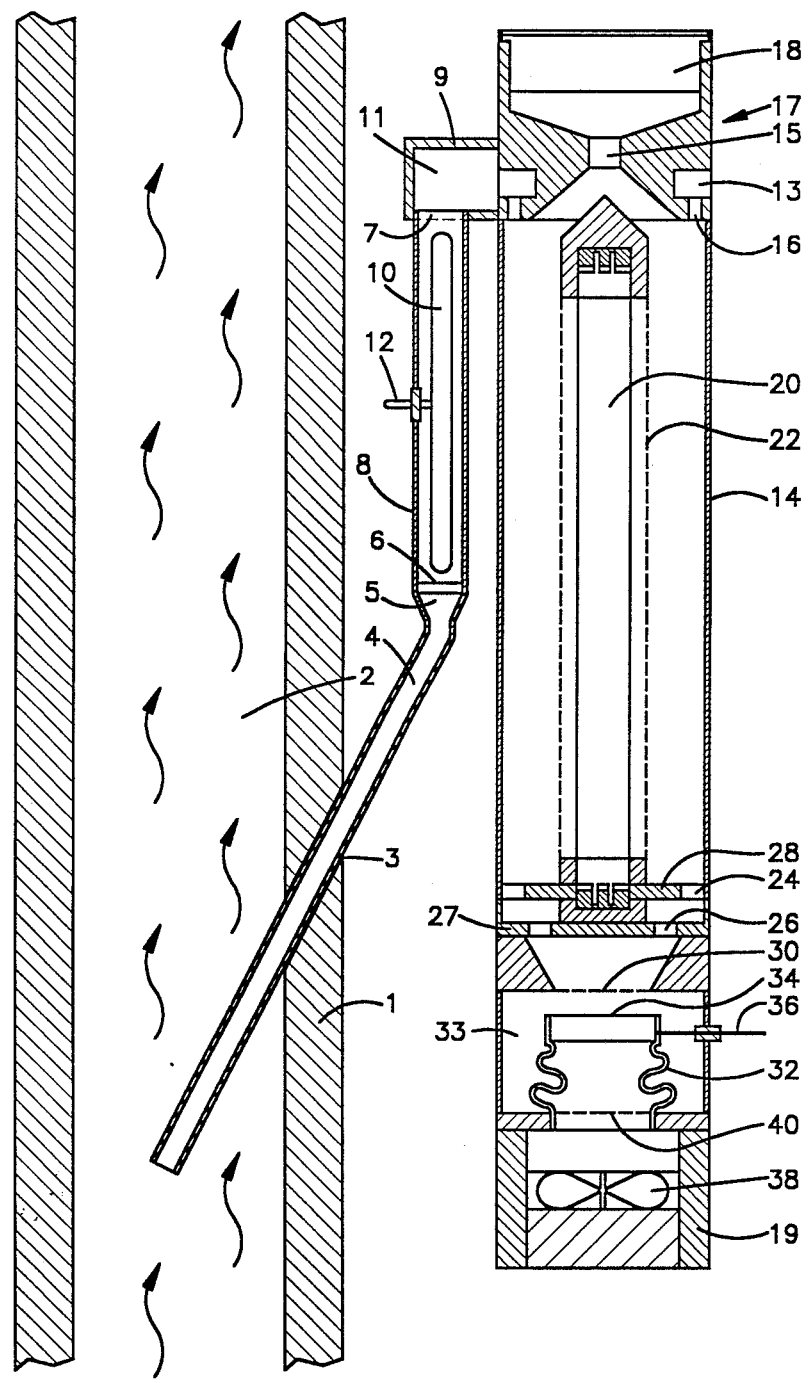

AUTOMATICALLY REGULATED COMBUSTION PROCESS

BACKGROUND OF THE INVENTION

1. Field of the Invention

It is a well known fact that wood, coal, natural gas, petroleum and other organic substances are burned in important amounts in private and commercial combustion plants as well as in thermal power engines. If too much air or oxygen is fed during the combustion process, a loss occurs because the excessive air carries off a substantial amount of heat. If too little air is fed, there is generated, besides soot, also the toxic carbon monoxide and furthermore hydrocarbons, among them some highly cancerogenic species as e.g. the benze-a-pyrene. The ever increasing contamination of our environment, particularly of the air we are breathing, with cancerogenic substances exhibits a very substantial menace to the population. In order to avoid any danger of explosion also occuring during the production of these harmful substances, particularly heating plants and automobiles without catalytic post-combustion have to be operated with a certain amount of excess air. On the other side it is not desirable at all to spend the valuable fuels unnecessarily by conducting a combustion process with a too great amount of excess air.

2. Prior Art

It is well known for a long time that the ratio between fuel and air, called the factor $\lambda$, plays an important role during the process of a combustion. Particularly the efficiency and the emission of contaminations of combustion engines and heating plants is determined by the factor $\lambda$. Exactly, the factor $\lambda$ is defined by the ratio $= n_{O_2}$ (really): $n_{O_2}$ (ideally).

Thereby $n_{O_2}$ (really) means the really fed amount of air or oxygen and $n_{O_2}$ (ideally) the amount of air or oxygen which would be required for a complete combustion of the fuel. In the case of automobiles without catalytic post-combustion and in the case of heating plants, the factor $\lambda$ must usually be in the region of 1.2 to ensure optimal operating conditions. If the factor $\lambda$ is 1.1, an emission of contaminations and the danger of explosions must be expected; if the factor $\lambda$ is 1.3, the efficiency is decreased. However the optimal $\lambda$-values are different from case to case. Among other, they depend on the type of the thermal engine and of the firing plant, respectively, as well as on the kind of the fuel to be used.

It is further known that the factor $\lambda$ may be automatically adjusted, e.g. by means of a zirconium oxide oxygen sensor. It was thereby possible to decrease the fuel consumption of a heating plant by 5 to 10% and, simultaneously, to substantially improve the exhaust gas rates. The disadvantage of the zirconium oxide oxygen sensor lies in the fact that its proper function is impaired under the influence of lead and other substances wich might be contained in the exhaust gas, and it can therefore be used only in conjunction with certain selected kinds of fuel.

An electrode exposed to the exhaust gas must be protected by means of porous ceramic material; there is always a danger that the electrode will be contaminated. Furthermore, the diffusion of $O_2$ through the ceramic material is comparatively slow, particularly at lower temperatures, resulting in the fact that the control or regulation cycle to be realized by means of such an electrode becomes correspondingly slow as well. In addition it should be noted that a switching signal which is independent of the temperature is offered only if the factor $\lambda$ has the value of 1.0. This means that, in the case of combustion plants and automobiles without a catalytic post-combustion and operating with an optimal $\lambda$-factor, any excess oxygen must be removed by adding a certain amount of $H_2$ by titration, before the exhaust gas is fed to the solid electrolytic sensor. This requires a mechanism which is comparatively complex and thereby expensive which could be installed only in big combustion plants up to now.

OBJECTS OF THE INVENTION

It is therefore an object of the invention to provide a combustion process incorporating an automatic regulation of the combustion by means of a continuous adjustment of the factor $\lambda$, i.e. by continuously adjusting the ratio between fuel and air required for the combustion, in order to improve the efficiency of combustion and heating plants as well as of automobile engines and in order to reduce the emission of contaminations with the exhaust gases.

It is a further object of the invention to provide a combustion process which is very simple and reliable and which does not require the provision of complicated and expensive equipment to operate it in the desired manner.

It is a still further object of the invention to provide a combustion process wich can easily be adapted to different kinds of fuel without the need of changing or adjusting any equipment required for the regulation or control of the combustion.

SUMMARY OF THE INVENTION

The present invention is based on the fact that not-completely burned, i.e. oxidizable substances or radicals are present in the exhaust gas if the combustion process takes place with insufficient air supply. Such substances have, as should be well known to anybody skilled in the art, the tendency to emit electrons, i.e. the energy required for the exitation of an electron is comparatively low. In order to prove the existence of these substances or radicals, use is made of the known method of electrically charging suspended particles or aerosols by means of photoemission of electrons, as it is basically described in "Atmospheric Environment, Vol.17, No.3, pp.655 to 657, 1983", and in "J.Appl.Phys. 53(5), May 1982, pp.3787 to 3791". By means of the photoelectric charging, it is especially possible to prove the existence of extremely fine suspended particles, which cannot be detected by optical means, and which have a low photoelectric threshold, efficiently and selectively, i.e. also in the presence of other particles and materials. The existence of the said particles in the exhaust gas of a combustion process may be interpreted as a signal indicating that the ratio of oxygen to fuel is to low and may may be used thereby to regulate the $\lambda$-factor.

Based on these facts, the invention provides a combustion process in which a fuel is mixed with an oxygen-containing gas in an adjustable ratio and the fuel-gas-mixture is burned, thereby producing an exhaust gas. This exhaust gas or at least a part thereof is collected and exposed to an ultra violet radiation source, thereby generating positive and negative charge carriers in said exhaust gas by means of a photoelectric charge separation process. Now these positive or these negative charge carriers or both of them are to produce a measurement value which reflects the amount of the charge of said positive and/or said negative charge carriers. From this measurement value a control signal is derived which subsequently is used to adjust said ratio of said oxygen-containing gas and said fuel to an optimal value in response to said control signal.

It has been noted that at least some of the suspended particles with low photoelectric threshold survive when the exhaust gas is cooled below the thawing point. Therefore it may be advantageous to cool at least that amount of the exhaust gas which is exposed to said ultra violet radiation source prior to being subjected to such radiation. Preferably the cooling is effected below the thawing point, whereby the liquid or misty condensates thereby generated are removed prior to exposing said exhaust gas to said ultra violet radiation source. It is understood that larger particles, i.e. approximately from 1 μm upwards, hardly can be charged in view of the backdiffusion of the photoelectrons. Thereby they can be removed prior to being photoelectrically charged by means of a comparatively coarse filter in order to avoid a contamination of the sensing or detecting means.

It may be furthermore advantageous to remove already charged suspended particles from said exhaust gas prior to exposing said exhaust gas to said ultra violet radiation source.

In order to prevent any parts susceptible to contamination, corrosion etc. as e.g. the ultra violet radiation source, electrical isolators etc. from a contact with the exhaust gas, at least a part of the exhaust gas can be fed with a photoelectrically inert, i.e., particle-free gas prior to exposing said exhaust gas to said ultra violet radiation source. Said photoelectric inert gas may be normal or pre-cleaned air.

If it is desired to record only a certain charge group or a certain size group or an excerpt from the size spectrum of the positive and/or negative charge carriers by the measurement means, it may be desirable that said positive and said negative charge carriers generated by said photoelectric charge separation process are sorted according to their size and then brought to the measurement means. Such sorting may be performed by means of inertial precipitation by diffusional precipitation and-/or by means of electrostatic precipitation.

The relative or absolute amount of said positive and negative charge carriers generated by the photoelectric separation process and/or the relative or absolute value of the current generated by the charge on these carriers and serving as said measurement value can be varied with reference to the combustion process and/or with reference to the fuel used in the combustion process. Therefore, a number of different possibilities exist:

Said variation is effected by changing the photon energy or the photon energy spectrum of the ultra violet radiation source; or the intensity and/or the time duration of the ultra violet radiation acting on the exhaust gas is varied; or the velocity and/or the volume of the part of the exhaust gas exposed to said ultra violet radiation is varied.

It may be assumed that such very fine particles or aerosols suspended in the exhaust gas with a low photoelectric threshold are generated by a process including a shell-like growth of the particles. Thereby, firstly a non-volatile core of the particles consisting of coal or ash is built-up within the hottest regions of the combustion. During the displacement of these cores to the cooler zones the more volatile hydrocarbons and their radicals condense on these cores as for they are present due to an insufficient supply of oxygen. The hydrocarbon condensates either lower the photoelectric threshold of the particles or have a lower ionisation potential themselves, so that the agglomerate is electrically charged upon being exposed to an ultraviolet radiation. Thereby it is in a position to generate a corresponding electric signal in a suitable detector means.

It is important to note that particularly the less stable and therefore especially toxic hydrocarbons and their fragments easily emit electons when condensed on particles; they can thereby be detected and analyzed effectively and with an incredibly high sensitivity. Under certain circumstances, only a fraction of the surface of an ultra-fine, not yet visible particle has to be covered by a one atom thick layer of the said unstable hydrocarbons in order to enable such a particle to be photoelectrically charged.

BRIEF DESCRIPTION OF THE DRAWING

The enclosed drawing shows a schematic diagram of a control means in a sectional view which may be used in performing the combustion process according to the present invention. In the following, one example of performing the process will be further described, with reference to this drawing.

DESCRIPTION OF A PREFERRED EMBODIMENT

An installation as shown in the drawing is particularly suitable for the control and regulation of a heating plant using oil as a fuel and is intended to adjust the λ-factor, i.e. the ratio of air to fuel to be burned.

A certain amount of exhaust gas is picked-up from the flue 2 by means of an intake pipe 4. The intake pipe 4 is fixedly inserted into an opening 3 of the wall 1 of the flue 2. The pipe 4 has, in accordance with the selected aspiration speed, such a length that the exhaust gas, having left the flue 2, has cooled down substantially to ambient temperature. As can be seen from the drawing, the intake pipe 4 is not horizontally arranged, thereby enabling eventually occuring condensates to drop back into the interior of the flue 2.

A cylindrical, tubular chamber 8 adjoins the intake pipe 4 and comprises a filter means 6 intended to remove coarse particles from the exhaust gas and being arranged in the region of its intake opening 5, i.e. at its lower end, where the intake pipe 4 is connected to the tubular chamber 8. A metallic cylindrical member 10 is provided in the interior of the tubular chamber 8 and connected thereto by means of electrically insulating fastening members (not shown in the drawing). The tubular chamber 8 comprises further an electrical connector 12 which is electrically connected to the cylindrical member 10, but insulated from the wall of the chamber 8. If a DC voltage is applied to the connector 12 and thereby to the cylindrical member 10, with reference to the wall of the chamber 8, an electric field is generated which is directed perpendicular to the flow of the exhaust gas passing through the interior of the chamber 8 and which filters out any charged particles which might be present in the exhaust gas flow.

The upper end of the chamber 8 has an outlet aperture 7 comprising a flange 9 connected to the upper part 17 of a processing chamber 14. The interior 11 of the flange 9 communicates with an annular distribution chamber 13 which communicates by means of a plurality of circularly arranged inlet apertures 16 with the interior of the processing chamber 14. The apertures 16 are distributed along the region of the periphery of the upper part 17.

The exhaust gas flow thus pre-processed leaves the chamber 8 through the outlet aperture 7, passes the flange 9 and enters the annular chamber 13. Said upper part 17 of the processing chamber 14 further comprises a central aperture 15 as well as an air filter 18 arranged thereabove. The aperture 15 opens into the interior of the processing chamber 14.

Under the influence of a fan 38 provided in the lower part 19 of the processing chamber 14, the pre-processed exhaust gas in the annular chamber 13 enters the chamber 14 via the apertures 16, and fresh air, pre-cleaned by the filter 18, enters the chamber 14 via the central aperture 15. The exhaust gas flow and the fresh air flow are mixed in the region of the inlet of the processing chamber 14.

The mixture of exhaust gas and fresh air now flows laminarly through the processing chamber 14. In its center, a coaxially mounted light source 20 is provided. This light source 20 may be an elongate, usual low pressure mercury lamp generating substantially ultra violet light with an energy of 4.9 eV. An electrically conducting grid 22 surrounds the light source 20 in order to shield it and to block any electric interference fields that might occur. Due to the laminar flow of the gas flow charged with suspended particles along the innner wall of the processing chamber 14 any contamination of the light bulb 20 is prevented.

Under the influence of the ultra violet light generated by the bulb 20 photoelectrons are emitted from the particles in the exhaust gas flow if their threshold amounts to less than 4.9 eV. The grid 22 and the metallic wall of the processing chamber 14 are connected to a AC power source. The emitted electrons and the small ions eventually formed therefrom reach the grid 22 or the wall 14, thereby serving as electrodes, and are removed from the exhaust gas flow by absorption or neutralisation. The amplitude and the frequency of the AC power source applied to the electrodes 14 and 22 are adjusted in such a way that the remaining positively charged particles only perform a small oscillating motion with a very small amplitude so that most of them stay in the exhaust gas flow. This behavior is based on the fact that they have a smaller electric mobility than the electrons and the small ions formed therefrom.

The suspended particles are removed from the ionisation path by the exhaust gas flow through a plurality of holes 24 and 26 provided in two disc-shaped locking members 27 and 28 for the light source 20. The holes 24 and 26 are circularly arranged along the periphery of the two disc-shaped members 27 and 28, respectively, on circles with different diameter, i.e. in staggered relationship, thereby providing a light trap preventing the radiation generated by the bulb 20 from leaving the interior of the processing chamber 14.

Now the exhaust gas containing the particles flows through an electric shielding grid 30 into a filter 34 which is supported by an electrically insulating mounting member 32. The filter 34 retains all particles which have been suspended in the gas flow. If some of the particles are positively charged, it is possible to obtain a positive electric charge or a positive electric current at a connector 36 insulatingly connected to the wall of the processing chamber 14 and conductingly connected to the filter 34. The charge or current thus obtained may be amplified and serves for the continuous or stepwise, automatic or manual regulation of the λ-factor.

The fan 38 provides the necessary flow, on the one hand of the ambient air to be cleaned by the filter 18, on the other hand of the exhaust gas through the intake pipe 4. The fan 38 is separated from the filter chamber 33 by a shielding grid 40.

The mixture ratio between exhaust gas and fresh air is influenced to a great extent by the length of the intake pipe 4 and by the diameter thereof. It is within the scope of the knowledge of a person skilled in the art to properly adjust these parameters, as well as the partial flow of the exhaust gas and/or the intensity and/or the size of the low pressure mercury light source 20, and finally also the diameter of the processing chamber 14. It is important is that the signal generated by the charged particles is high enough, i.e. that it can be reliably measured and further developed in a known control means, in order to provide a proper adjustment of the λ-factor.

The process according to the present invention may be modified in different respects. In the following, just a few further possibilities to perform the process according to the invention are listed. It is understood, that in every example of the process, a fuel is mixed with an oxygen-containing gas in an adjustable ratio, said fuel-gas-mixture is burned and thereby an exhaust gas is produced, at least a part of said exhaust gas is collected and exposed at least intermittently to an ultra violet light source, thereby generating positive and negative charge carriers in said exhaust gas by means of a photoelectric charge separation process.

In a first mode, said positive charge carriers are deposited on a first electrode and said negative charge carriers on a second electrode. Then the amount of charge collected by at least one of said first and second electrode is detected and said ratio of said oxygen-containing gas and said fuel is adjusted to an optimal value in response to the measured amount of charge collected by at least one of said first and second electrode.

Thereby either the charge collected by said first electrode is detected and said ratio of said oxygen-containing gas and said fuel is adjusted to an optimal value in response to said measured amount of charge collected by said first electrode, or the charge collected by said second electrode is detected and said ratio of said oxygen-containing gas and said fuel is adjusted to an optimal value in response to said measured amount of charge collected by said second electrode, or the charge collected by said first electrode and the charge collected by said second electrode is detected, said two measurement values being combined into a control signal, and said ratio of said oxygen-containing gas and said fuel is adjusted to an optimal value in response to said control signal.

In a second mode the ohmic conductivity related to said positive and said negative charge carriers is determined without removing said carriers from the gas, and a control signal is derived from said measurement of the conductivity. The ohmic conductivity may be determined, i.e., by applying an alternating voltage between electrodes. The alternating current induced by the resulting carrier motion is the current component which is in phase with the voltage. The ohmic conductivity is the ratio of said voltage and said current component. Then said ratio of said oxygen-containing gas and said fuel is adjusted to an optimal value in response to said control signal.

In a third mode the negative charge carriers are removed from said exhaust gas and the conductivity of said positive charge carriers thus remaining in said exhaust gas is measured. Then a control signal is derived from said measurement of the conductivity of said remaining positive charge carriers, and the ratio of said oxygen-containing gas and said fuel is adjusted to an optimal value in response to said control signal.

It should be finally emphasized that the process according to the present invention may be used in a plurality of other applications, e.g. in the field of automotive engines or other thermal motors. It is understood that the apparatus and control means will have to be changed accordingly.

What we claim:

1. A combustion process comprising the steps of mixing an organic fuel with an oxygen-containing gas in an adjustable ratio, burning said fuel-gas mixture and thereby producing an exhaust gas containing a plurality of finely dispersed aerosol particles, collecting at least a part of said exhaust gas containing said finely dispersed aerosol particles and exposing said collected exhaust gas and thereby also said finely dispersed aerosol particles at least intermittently to an ultraviolet radiation source, thereby generating positive and negative charge carriers in said exhaust gas solely by means of photoelectrically charging said aerosol particles contained in said exhaust gas, detecting said positive or negative charge carriers to produce a measurement value which reflects the amount of charge of said positive or negative charge carriers, generating a control signal from said measurement value, and adjusting said ratio of said oxygen-containing gas and said fuel to an optimal value in response to said control signal.

2. A process according to claim 1, further comprising the step of cooling at least that amount of the exhaust gas which is exposed to said ultra violet radiation source prior to being subjected to ultraviolet radiation.

3. A process according to claim 2, wherein said amount of exhaust gas is cooled below the thawing point, and further comprising the step of removing the condensates thereby generated prior to exposing said exhaust gas to said ultra violet radiation source.

4. A process according to claim 1, further comprising the step of filtering-out particles suspended in said exhaust gas, which have a certain size range, from said exhaust gas prior to exposing said exhaust gas to said ultra violet radiation source.

5. A process according to claim 1, further comprising the step of removing already charged suspended particles from said exhaust gas prior to exposing said exhaust gas to said ultra violet radiation source.

6. A process according to claim 1, further comprising the step of feeding at least a part of said exhaust gas with a photoelectrically inert gas prior to exposing said exhaust gas to said ultra violet radiation source, in order to prevent any parts susceptible to contamination, corrosion etc. as e.g. the ultra violet radiation source, electrical insulators etc. from a contact with the exhaust gas.

7. A process according to claim 6, wherein said photoelectric inert gas is ambient or pre-cleaned air.

8. A combustion process comprising the steps of mixing an organic fuel with an oxygen-containing gas in an adjustable ratio, burning said fuel-gas-mixture and thereby producing an exhaust gas containing a plurality of finely dispersed aerosol particles, collecting at least a part of said exhaust gas containing said finely dispersed aerosol particles and exposing said collected exhaust gas and thereby also said finely dispersed aerosol particles at least intermittently to an ultraviolet radiation source, thereby generating charge carriers of positive and negative polarity in said exhaust gas by means of photoelectrically charging said finely dispersed aerosol particles contained in said exhaust gas, depositing said charge carriers of at least one of both polarities on at least one corresponding electrode, detecting the amount of charge collected by said electrode, and adjusting said ratio of said oxygen-containing gas and said fuel so as to at least approximate an optimal value in response to the measured amount of charge collected by said electrode.

9. A combustion process comprising the steps of mixing an organic fuel with an oxygen-containing gas in an adjustable ratio, burning said fuel-gas mixture and thereby produced an exhaust gas containing a plurality of finely dispersed aerosol particles, collecting at least a part of said exhaust gas containing said finely dispersed aerosol particles and exposing said collected exhaust gas and thereby also said finely dispersed aerosol particles at least intermittently to an ultraviolet radiation source, thereby generating charge carriers of positive and negative polarity in said exhaust gas by means of photoelectrically charging said finely dispersed aerosol particles contained in said exhaust gas, depositing said charge carriers of at least one of both polarities on at least one corresponding electrode, detecting the amount of charge collected by said electrode, and adjusting said ratio of said oxygen-containing gas and said fuel so as to at least approximate a minimum amount of hydrocarbons in said exhaust gas in response to the measured amount of charge collected by said electrode.

* * * * *

UNITED STATES PATENT AND TRADEMARK OFFICE
CERTIFICATE OF CORRECTION

PATENT NO. : 4,959,010

DATED : September 25, 1990

INVENTOR(S) : Heinz Burtscher, Andreas Schmidt-Ott, and Hans-Christoph Siegmann

It is certified that error appears in the above-identified patent and that said Letters Patent is hereby corrected as shown below:

Column 8, Line 34, Claim 9, change "produced" to --producing--.

Signed and Sealed this

Twelfth Day of May, 1992

Attest:

DOUGLAS B. COMER

*Attesting Officer*     Acting Commissioner of Patents and Trademarks